United States Patent
Blick et al.

(10) Patent No.: US 11,698,363 B2
(45) Date of Patent: Jul. 11, 2023

(54) METHOD TO DETERMINE THE THROUGHPUT SPEED OF A PORE

(71) Applicants: Wisconsin Alumni Research Foundation, Madison, WI (US); UNIVERSITAT HAMBURG, Hamburg (DE)

(72) Inventors: Robert Blick, Hamburg (DE); Paul Gwozdz, Hamburg (DE); Abhishek Bhat, Madison, WI (US)

(73) Assignees: Wisconsin Alumni Research Foundation, Madison, WI (US); Universität Hamburg

( * ) Notice: Subject to any disclaimer, the term of this patent is extended or adjusted under 35 U.S.C. 154(b) by 619 days.

(21) Appl. No.: 16/632,296

(22) PCT Filed: Jul. 16, 2018

(86) PCT No.: PCT/IB2018/055250
§ 371 (c)(1),
(2) Date: Jan. 17, 2020

(87) PCT Pub. No.: WO2019/021108
PCT Pub. Date: Jan. 31, 2019

(65) Prior Publication Data
US 2021/0072220 A1    Mar. 11, 2021

Related U.S. Application Data

(60) Provisional application No. 62/537,530, filed on Jul. 27, 2017.

(30) Foreign Application Priority Data

Sep. 4, 2017 (LU) ................................. LU100392

(51) Int. Cl.
*G01N 33/487* (2006.01)
*C12Q 1/6869* (2018.01)
(Continued)

(52) U.S. Cl.
CPC ..... *G01N 33/48721* (2013.01); *C12Q 1/6869* (2013.01); *G01N 33/588* (2013.01);
(Continued)

(58) Field of Classification Search
None
See application file for complete search history.

(56) References Cited

U.S. PATENT DOCUMENTS 10,400,278 B2    9/2019  Davis et al.
2016/0077078 A1  3/2016  Huber et al.
(Continued)

FOREIGN PATENT DOCUMENTS

WO    2000009757 A1   2/2000
WO    2005017205 A2   2/2005

OTHER PUBLICATIONS

N.A.W. Bell, et al., "Direct measurements reveal non-Markovian fluctuations of DNA threading through a solid-state nanopore", arXiv preprint arXiv: 1607.04612, 5 pages, July (Year: 2016).*
(Continued)

*Primary Examiner* — J. Christopher Ball
(74) *Attorney, Agent, or Firm* — Quarles & Brady LLP (57) ABSTRACT

A method to determine the throughput speed v of a pore, comprising the steps of feeding, by means of a driving force F, a filiform calibration element through the pore, the calibration element having a plurality of markers spaced apart by known distances and configured to produce an interaction event that transmits a signal away from the pore upon interaction with the pore, detecting a plurality of interaction events, and determining a time interval $\Delta t$ between successive interaction events, and/or a frequency $\omega$ of interaction events.

12 Claims, 4 Drawing Sheets

(51) Int. Cl.
 *G01N 33/58* (2006.01)
 *G01N 27/447* (2006.01)
 *G01N 15/00* (2006.01)

(52) U.S. Cl.
 CPC .................. *G01N 27/44791* (2013.01); *G01N 2015/0065* (2013.01)

(56) References Cited

U.S. PATENT DOCUMENTS

2016/0122812 A1 5/2016 Huber
2017/0059547 A1 3/2017 Feng et al.

OTHER PUBLICATIONS

Plesa, et al., "Velocity of DNA During Translocation through a Solid State Nanopore," Nano letters 15.1 (2014); 732-737.
European Patent Office. Extended European Search Report and Written Opinion for application 18837884.8. dated May 3, 2021. 7 pages.
Branton, D., et al. "The potential and challenges of nanopore sequencing." Nature biotechnology 26.10 (2008): 1146-1153.
Wanunu, M., et al. "Electrostatic focusing of unlabelled DNA into nanoscale pores using a salt gradient." Nature nanotechnology 5.2 (2010): 160-165.

\* cited by examiner

METHOD TO DETERMINE THE THROUGHPUT SPEED OF A PORE

CROSS REFERENCE TO RELATED APPLICATIONS

This application is a U.S. National Stage of PCT Application No. PCT/IB2018/055250 filed on Jul. 16, 2018 which claims the benefit of U.S. Provisional Patent Application No. 62/537,530, filed on Jul. 27, 2017, and Luxembourg Patent Application No. LU100392, filed on Sep. 4, 2017, the entire contents of all of these applications are incorporated herein by reference in their entirety for all purposes.

The invention relates to the characterization of the throughput properties of nanopores and nanochannels that may, e.g., be used for sequencing biomolecules or for filtering mixtures of substances.

BACKGROUND

Since the inception of the first methods for sequencing DNA, remarkable strides have been made to improve the number of consecutive base pairs that can be read, while at the same time increasing the speed of the sequencing and reducing the amount of sample material needed for the sequencing. (H. Stranneheim, J. Lundeberg, "Stepping stones in DNA sequencing", Biotechnology Journal 2012, 7, 1063-1073, doi: 10.1002/biot.201200153) outlines the evolution of sequencing technologies.

Nanopore sequencing has recently emerged as a method that permits to sequence DNA with a very high throughput while at the same time not requiring a complicated preparation or even amplification of the sample. A measurement chamber is divided into a cis-chamber and a trans-chamber by a membrane with one or more nanopores (or nanochannels for that matter). Both the cis-chamber and the trans-chamber are filled with an electrolyte solution. The analyte DNA is supplied at least in one chamber. By applying a voltage between the cis-chamber and the trans-chamber, ions are drawn from one chamber through the nanopore into the other chamber, leading to an ionic current. When a base pair passes through the nanopore, the ionic current is altered by an amount that is different depending on which base pair (A, C, G or T) it is. (Y. Feng, Y. Zhang, C. Ying, D. Wang, C. Du, "Nanopore-based Fourth-generation DNA Sequencing Technology", Genomics Proteomics Bioinformatics 13 (2015), 4-16, doi: 10.1016/j.gbp.2015.01.009) gives a review.

Furthermore, nanopores are emerging as high-throughput filters that may, for example, separate water from salt and produce fresh water out of sea water in an energy-efficient way. (M. Heiranian, A. B. Farimani, N. R. Alum, "Water desalination with a single-layer MoS2 nanopore", Nature Communications 6:8618, doi: 10.1038/ncomms9616) provides an example.

For the design and manufacture of nanopores to suit these or other applications, it is important to be able to quantitatively study their throughput behavior.

OBJECTIVE OF THE INVENTION

It is therefore the objective of the present invention to permit a quantitative calibration of the throughput behavior of nanopores.

This objective is achieved by a measurement method, a filiform calibration element and a liquid solution comprising a plurality of filiform calibration elements. Further advantageous embodiments are detailed in the dependent claims.

DISCLOSURE OF THE INVENTION

The invention provides a method to determine the throughput speed $v$ of at least one pore. The term "pore" shall also comprise "channel". In the following, "pore" is used throughout for intelligibility.

In the course of this method, a filiform calibration element is fed through the pore by means of a driving force F. The calibration element has a plurality of markers spaced apart by known distances. The markers are configured to produce an interaction event that transmits a signal away from the pore upon interaction with the pore. The creation of the event may, for example, happen upon entry into, and/or exit from the pore. The creation of the event may also, for example, happen when the marker is at a specific place within the pore.

The filiform calibration element is preferably a thread-like elongate element that is may be bent but not stretched to a substantial extent, akin to, e.g., a sewing thread, a metal chain, or a metal cable. In this manner, the driving force F may ease the filiform calibration element into the pore by bending an end of it towards the pore and drawing this end into the pore, without changing the known distances between the markers along the length of the filiform calibration element.

A plurality of interaction events is detected. Subsequently, a time interval $\Delta t$ between successive interaction events, and/or a frequency $\omega$ of interaction events, is determined as a measure for the throughput velocity $v$.

The inventors have found that this allows, for the first time, a direct quantitative assessment of the throughput properties of pores, especially nanopores. Previously, the only indication of the throughput behavior was the macroscopic ionic current. This ionic current is reduced when a base pair passes through the pore and partially or completely blocks the pore. While the temporal behavior of the ionic current is certainly dependent on the throughput speed $v$ of the pore, it is not sufficient for unambiguously reconstructing this throughput speed $v$ in terms of a calibration standard. The blockage of the ionic current is not a sharp event that denotes a point in time, but rather a state that lasts for a time period as long as the base pair passes through the pore. During this time period, it is not possible to distinguish whether there is one or more than one object within the pore. By contrast, the interaction events according to the instant invention may be tuned to denote one particular moment of the interaction between the marker and the pore.

For example, the marker may be configured to hit a mechanical stop when entering the pore, transmitting a force signal through the filiform calibration element itself. In another example, the marker may be configured to optically interact with the pore, causing an increase or decrease in a detectable light intensity when the marker is in just the right place relative to the pore (the pore/channel can be possessing an optically active layer).

Therefore, in an especially advantageous embodiment of the invention, a condition for production of the event by a marker is fulfilled at most in an interval along the path that the marker follows when the filiform calibration element is fed through the pore, wherein the length of this interval is at most 20% of the length of the pore.

Specifically, the condition for production of the event may be configured so that it can be fulfilled only once for any given marker along the path it follows when the filiform calibration element is fed through the pore. For example, a mechanical stop may only be hit once and then it is overcome, or a condition for optical resonance may admit this resonance only for one relative spatial arrangement of the marker vis-à-vis the pore.

The evaluation of interaction events, which denote sharp points in time and are therefore suitable to calibrate a throughput speed v, may optionally be complemented with the monitoring of the temporal behavior of the ionic current.

In an especially advantageous embodiment of the invention, from the known distances on the one hand and from the time interval $\Delta t$ and/or the frequency $\omega$ on the other hand, the speed with which the filiform calibration element passes through the pore is determined as the throughput speed v. This throughput speed v is an absolute quantity that is not convolved with the driving force F.

In a further especially advantageous embodiment of the invention, the throughput resistance R of the pore is determined as a ratio of the speed v per unit of the driving force F. Specifically, the possibility to measure v as an absolute quantity allows to study the dependency of v on F. This dependency need not be linear for all values of F. Specifically, the dependence may qualitatively change to a nonlinear response at some point when F is increased.

In one advantageous embodiment of the invention, at least one increase in the mechanical resistance that the filiform calibration element experiences when moving through the pore is detected as an interaction event. The markers on the filiform calibration element may then be mechanical markers that are comparatively simple to fabricate, e.g., by means of tried-and-tested DNA origami. The mechanical resistance may, for example, be measured by means of a direct force measurement on the filiform calibration element. However, it may also, for example, be measured indirectly through a quantity of the mechanism that provides the driving force F, e.g., an electrical quantity: when there is a mechanical resistance, this mechanism may, e.g., need a higher voltage, or draw a higher current, to overcome this resistance.

In a further, especially advantageous embodiment of the invention, the intensity of light that is emitted from a marker is measured with a detector outside the pore, and at least one change of said intensity is detected as an interaction event. For example, a marker may be specifically configured to interact with the pore in a manner that when the marker is in a specific relative position with respect to the pore, the light that is emitted from the marker is either notably amplified or notably attenuated, providing a sharp cue in the intensity signal and increasing the accuracy with which the throughput speed v may be determined. To this end, the nanopore/nanochannel may be provided with an antenna structure, i.e., a plasmonic or similar antenna.

Therefore, preferably, the change of the intensity is an increase of the intensity that results from an amplification of the light by the inner wall of the pore, or a decrease of the intensity that results from an extinction of the light produced by the inner wall of the pore. Again, EM- and RF-antenna structures may be used as possible tuning mechanisms.

Optical (in general electrodynamic) detection of the interaction has the further advantage that by appropriately choosing a wavelength of the light that is emitted from the marker, the signal resulting from the interaction between the marker and the pore may be easily distinguished from other signals. By contrast, if the only signal that is available is the ionic current through the pore, the portion related to an interaction between the marker and the pore is convolved with a lot of other contributions. It is also worth noting that the detection bandwidth of optical detectors is several orders of magnitude larger than the detection bandwidth of current detectors: if they are sensitive enough to detect some pA, they are limited to a maximum of some nA.

In addition, the reliance of the prior art on the ionic current necessitates that the driving force F for the filiform calibration element is an electrostatic force. By contrast, according to the instant invention, the choice of the type of driving force F is not so limited. For example, the driving force F may, alternatively or in combination, also comprise a pressure gradient or a concentration gradient.

In an especially advantageous embodiment of the invention, the feeding of the filiform calibration element through the pore specifically comprises contacting the pore with a liquid solution comprising a plurality of filiform calibration elements. In this manner, it is not required to individually manipulate a filiform calibration element using microscopic techniques. Rather, using purely macroscopic handling, the solution may be supplied to the pore, and the driving force F itself may be used to draw at least one of the filiform calibration elements into the pore.

This embodiment is particularly advantageous in a case where more than one pore is present. For example, a DNA sequencing apparatus may comprise several pores to parallelize the sequencing, and/or a filter for the separation of salt from water molecules may comprise very many pores to achieve a maximum throughput of water per unit area.

As detailed above, in an especially advantageous embodiment of the method, the interaction events are optical events. To this end, the invention provides a filiform calibration element that is configured to pass through a pore of at most 5 μm diameter. The filiform calibration element comprises a plurality of light sources that are configured to absorb excitation light of a first wavelength $\lambda_1$ and to emit light of a second wavelength $\lambda_2$ in response to said excitation light. These light sources serve as markers.

The inventors have found that such a calibration element may generate signals at the second wavelength $\lambda_2$ that particularly sharply and specifically indicate an interaction event between a marker and a pore: The pore and the marker may be tuned to each other so that there is an amplifying resonance between the marker and the pore at the second wavelength $\lambda_2$ when the marker and the pore are in a specific spatial arrangement to each other. For example, there may be resonance when the marker has proceeded to a certain depth within the pore. Such an event may then be detected easily and sharply by monitoring the signal at wavelength $\lambda_2$. This signal may, e.g., be separated from the signal at wavelength $\lambda_1$ by spectral filtering. However, this is not mandatory. If, e.g., the pair of wavelengths $\lambda_1$ and $\lambda_2$ is preferably selected so that light of the wavelength $\lambda_1$ is never amplified in the same manner as light of the wavelength $\lambda_2$, the amplifying resonance at wavelength $\lambda_2$ may far outweigh a background of wavelength $\lambda_1$ in the total intensity emitted from the area of the pore.

In an especially advantageous embodiment of the invention, the light sources are quantum dots. These light sources convert a rather large portion of light received at the first wavelength $\lambda_1$ to the second wavelength $\lambda_2$ even if they are of a very small size, much smaller than the wavelengths $\lambda_1$ and $\lambda_2$, that fits through very small pores.

In an especially advantageous embodiment of the invention, the light sources are bound to a strand comprising at least one of: a DNA-like structure, a polymer, or a fluorophore. These structures may be made flexible for bending, but at the same time rigid against changes of their length. At the same time, these structures are sufficiently regular so that light sources may be attached to them spaced apart by known distances in a self-organized manner.

In a further especially advantageous embodiment of the invention, the light sources are quantum dots, the strand is a DNA strand with at least one sticky end, and at least one quantum dot is coupled to a counterpart of said sticky end by means of a thiol group. Said counterpart is in turn attached to said sticky end of the DNA strand, or bound to other sites along the DNA strand. This can be determined through ligation. A filiform calibration element having this structure may be manufactured very easily employing only a few reactions, allowing for a high yield.

Most preferably, the filiform calibration element is configured to pass through a pore of at most 200 nm diameter. Pore sizes in this range are the most interesting pore sizes both for DNA sequencing and for filtering.

In a further especially advantageous embodiment of the invention, the filiform calibration element is further functionalized to be electronegative, so as to facilitate the driving of the filiform calibration element through the pore by means of an electrostatic driving force F. Specifically, such a driving force may then guide an end of the filiform calibration element into the pore in the first place, so that further application of the driving force F will then feed the markers through the pore one by one.

Preferably, filiform calibration elements are stored and marketed in a liquid solution comprising a solvent. Such a solution is immediately usable to determine the throughput speed v of the pore. Therefore, in accordance with the disclosure regarding the filiform calibration element, the instant invention also relates to a liquid solution as a tool for determining the throughput speed v of at least one pore. The solution comprises a solvent and a plurality of filiform calibration elements according to the invention.

Preferably, the solution comprises buffered KCl. The concentration can be tuned depending on the desired experimental conditions.

Preferably, the concentration of the solution is up to 1M KCl. Typical filiform calibration element concentrations can range from a couple of fM to hundreds of nM. These concentrations can be increased significantly if an array of pores is used for the experiments.

DESCRIPTION OF THE FIGURES

In the following, the invention is illustrated using Figures without any intention to limit the scope of the invention. The Figures show.

Figure 1:
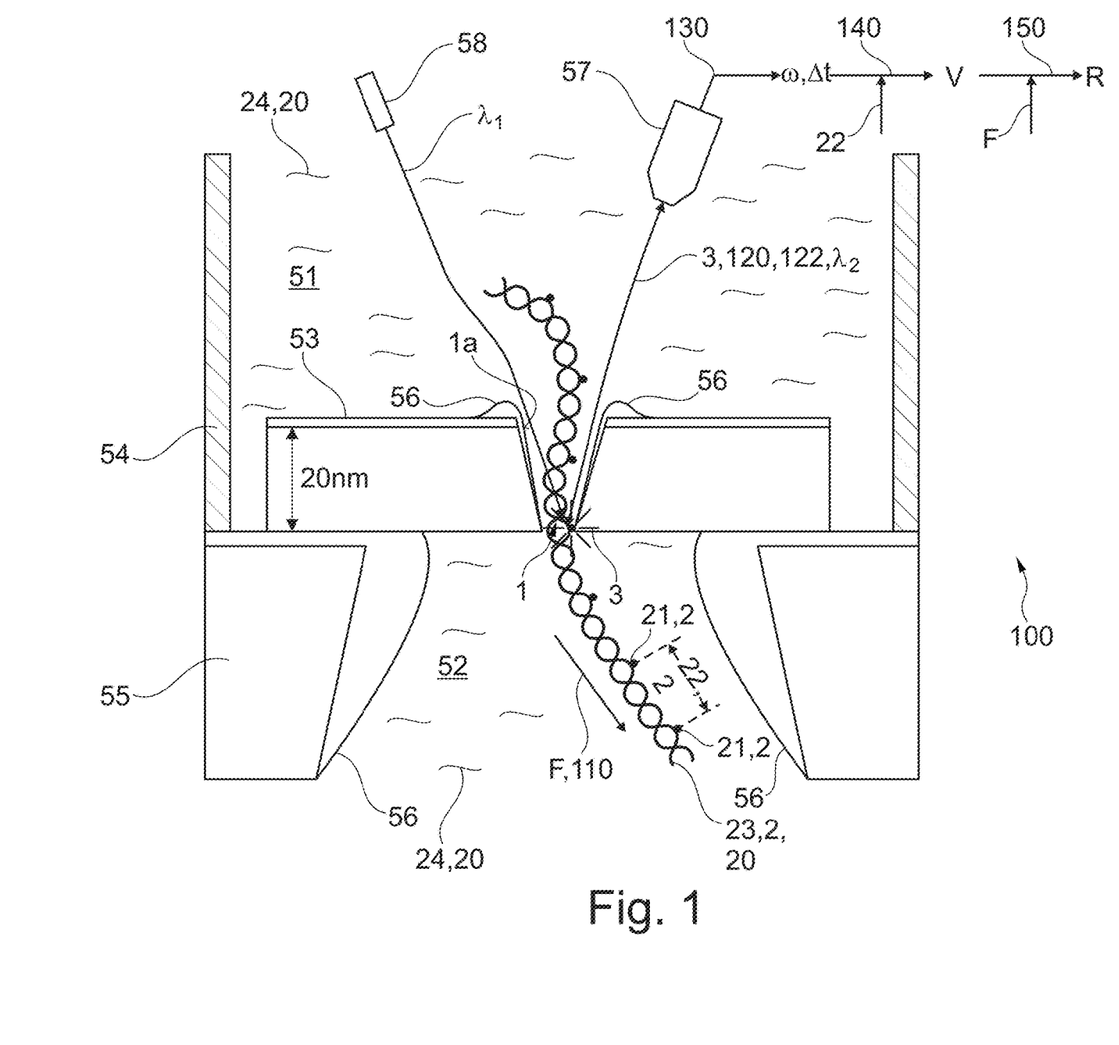
FIG. 1: Exemplary embodiment of the method 100 according to the invention.

FIG. 1 illustrates an exemplary embodiment of the method 100 according to the invention. FIG. 1 is schematic and not drawn to scale. A glass base 55 and a cylindrical wall 54 define a space that is divided into a trans-space 51 and a cis-space 52 by a solid-state membrane 53. Seals between the glass base 55, the cylindrical wall 54 and the solid-state membrane 53 are formed by polymethyldisiloxane (PDMS) 56. The solid-state membrane 53 comprises a conical pore 1 with an inner wall 1a. Part of the inner wall 1a of the pore 1, and the surrounding area on the surface of the membrane 53, is covered by PDMS 56 as well as a result of the fabrication process.

Both the trans-space 51 and the cis-space 52 are filled with a solution 20 that comprises a solvent 24 and filiform calibration elements 2. Only one filiform calibration element 2 is shown in FIG. 1 for clarity.

The filiform calibration element 2 comprises a DNA-like strand 23 to which a plurality of quantum dots 21 as markers are attached, spaced apart by known distances 22 along the length of the strand 23. For reasons of legibility, only two quantum dots 21 are labelled with reference signs in FIG. 1, and the distance 22 is indicated only once as well.

In step 110 of the method 100, the filiform calibration element is fed and pulled through the pore 1 in the membrane 53 by means of a driving force F. At the same time, the inside of the pore 1 is irradiated with light of wavelength $\lambda_1$ by a laser 58. Every quantum dot 21 that happens to be irradiated with the light of wavelength $\lambda_1$ will be excited to emit light of wavelength $\lambda_2$ in return. When the quantum dot 21 reaches the bottom of the pore 1, a resonance condition is fulfilled, and the interaction with the inner wall 1a of the pore 1 results in a drastic amplification of the light of wavelength $\lambda_2$ that is emitted from the quantum dot 21. This amplification is used as the interaction event 3 to calibrate the throughput speed v.

This amplified light is detected by a detector 57 in step 122. As per step 120, a plurality of interaction events 3 is detected. In step 130, a time interval $\Delta t$ between successive interaction events, and/or a frequency $\omega$ of interaction events 3, is determined. In step 140, the desired throughput speed v is evaluated from the time interval $\Delta t$, and/or from the frequency $\omega$, in combination with the known distance 22 between any two quantum dots 21. Optionally, in step 150, the throughput resistance R may be determined from the throughput speed v in combination with the amount of the driving force F.

Figure 2:
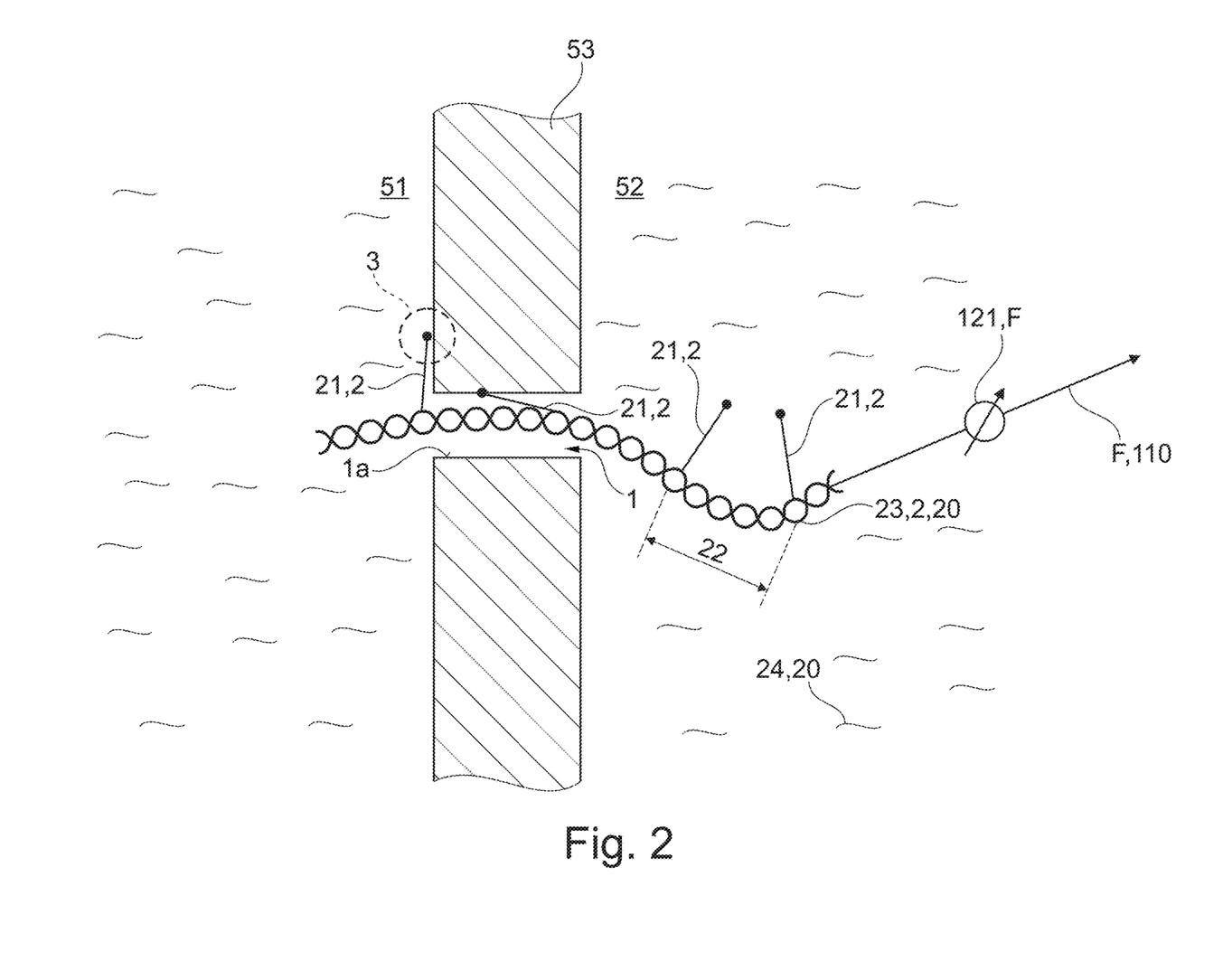
FIG. 2: Mechanical interaction 3 between markers 21 and the inlet of the pore 1.

FIG. 2 illustrates a different possible interaction 3 between markers 21 on a DNA-like strand 22 that may be used to calibrate the throughput velocity v of a pore 1 in a membrane 53. Akin to FIG. 1, the membrane 53 separates a trans-space 51 and a cis-space 52. The filiform calibration element 2 is pulled through the pore 1 from the trans-space 51 into the cis-space 52 by applying a driving force F, which is at the same time measured. Each time one of the markers 21 hits the entrance of the pore 1, it produces a mechanical resistance that sends a force signal through the strand 22 to the measurement instrument that is used to measure the driving force F. This is the interaction event 3 that is used to denote precise points in time where a marker 21 is exactly at the entrance of the pore 1, and that can be detected in step 121 of the method 100. Once the mechanical resistance has been overcome by the driving force F, the marker is flipped over and slides against the inner wall 1a of the pore 1 with only little resistance. After having passed the pore 1, the marker 21 is flipped back to its previous orientation perpendicular to the strand by means of a restoring force.

Figure 3:
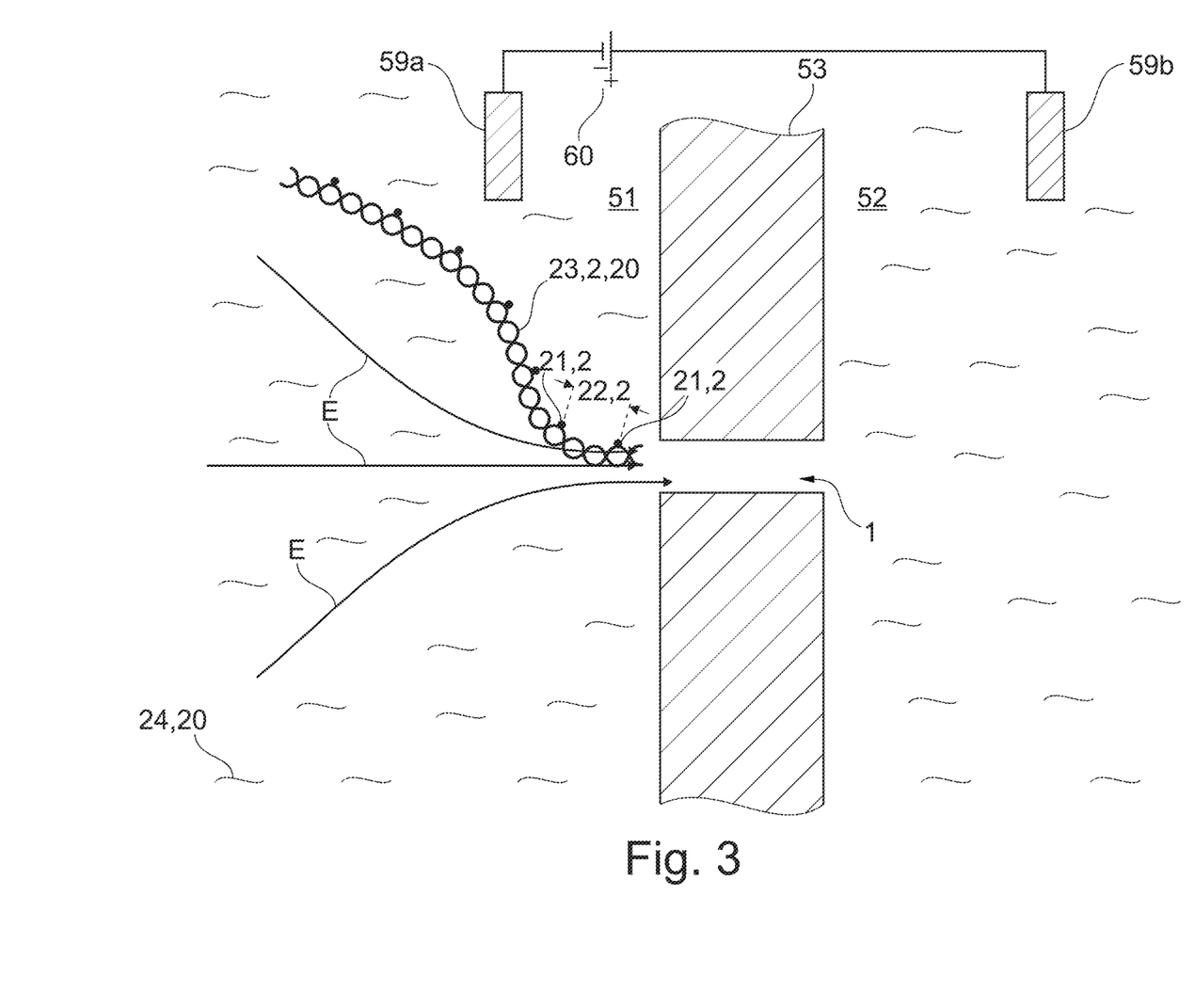
FIG. 3: Easing of an electronegative strand 22 into the pore 1 by means of an electric field E.

FIG. 3 illustrates how a filiform calibration element 2 that is floating in a solvent 20 may be eased into a pore 1. Between the trans-space 51 and the cis-space 52, a voltage is applied from a voltage source 60 by means of electrode 59a in the trans-space 51 and electrode 59b in the cis-space 52. The field lines of the electric field E converge on the pore 1 and re-orient the electronegative strand 22 of the filiform calibration element 2 so that its end will be pulled into the pore 1 by the electric field E.

Figure 4:
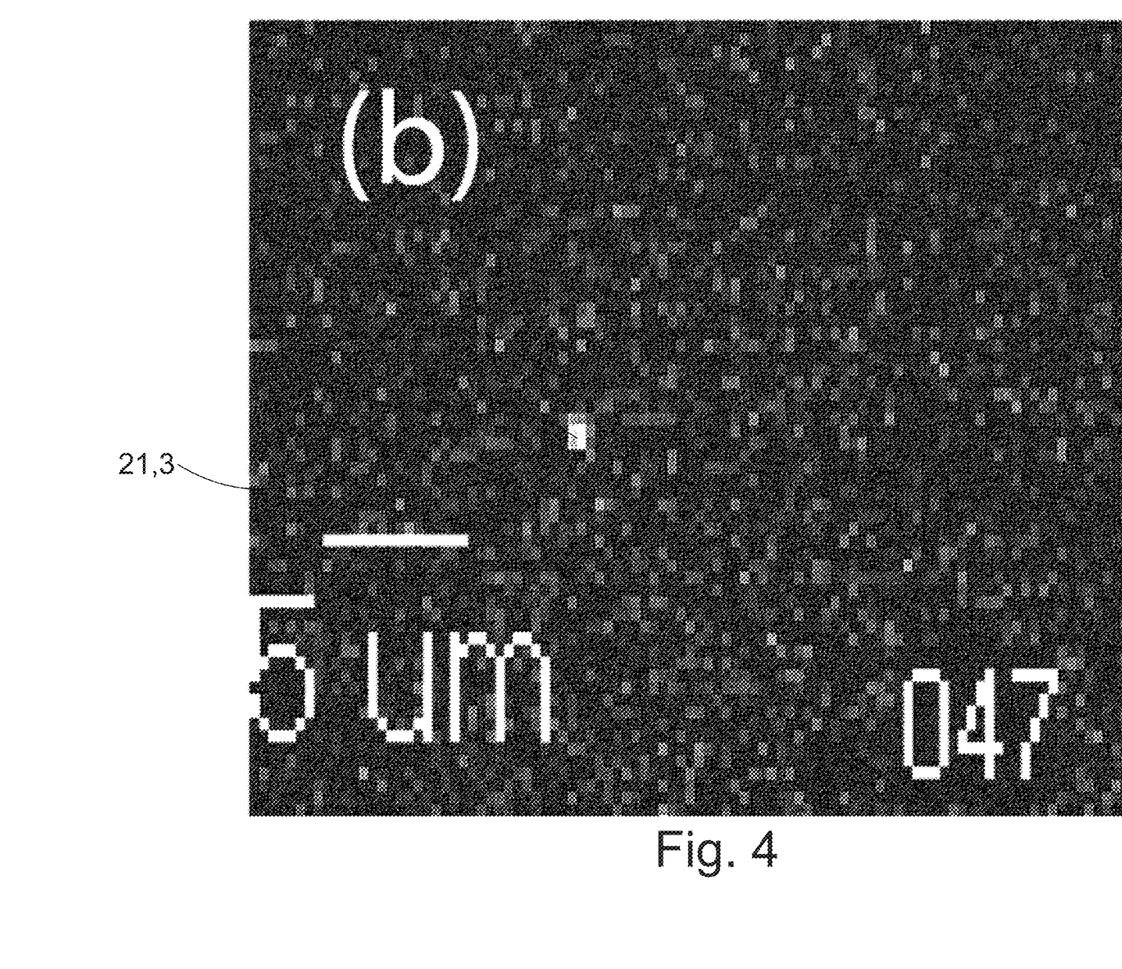
FIG. 4: Detection of a single quantum dot 21 with a macroscopic detector 57.

FIG. 4 is a real measurement result acquired with a macroscopic detector 57 as illustrated in FIG. 1. The detector 57 is sensitive to the wavelength $\lambda_2$ of the light that is emitted by the quantum dot 21. Its sensitivity is set so that the light intensity emitted from a quantum dot 21 is only noticeable if an interaction event 3 is occurring at the bottom of the pore 1 and the light emitted from the quantum dot 21 is amplified accordingly, as illustrated in FIG. 1. Therefore, it does not matter that the quantum dot 21 is much smaller than the wavelength $\lambda_2$. The diffraction limit may dictate that two or more quantum dots 21 with comparable light intensities cannot be distinguished from one another, but this does not preclude the detection of one single sufficiently intense light source.

Only three field lines of the electric field E are exemplarily drawn in FIG. 3 for clarity.

LIST OF REFERENCE SIGNS 1 pore
1a inner wall of pore 1
2 filiform calibration element
20 solution, comprising filiform calibration elements 2
21 markers of filiform calibration element 2
22 spacing between markers 21
23 strand of filiform calibration element 2
24 solvent
3 interaction event
51 trans-space
52 cis-space
53 membrane, comprising pore 1
54 cylindrical wall
55 glass base
56 polymethyldisiloxane (PDMS)
57 detector for light of wavelength $\lambda 2$
58 laser for light of wavelength $\lambda 1$
59a electrode in trans-space 51
59b electrode in cis-space 52
60 voltage source
E electric field
F driving force
$\lambda_1$ first wavelength, emitted by laser 58 to excite marker 21
$\lambda_2$ second wavelength, emitted by marker 21
R throughput resistance of pore 1
$\Delta t$ time interval between interaction events 3
v throughput speed of pore 1
$\omega$ frequency of interaction events 3
100 method
110 feeding filiform calibration element 2 through pore 1
120 detecting interaction events 3
121 detecting increase in mechanical resistance as interaction event 3
122 detecting change in light intensity as interaction event 3
130 determining time interval $\Delta t$ and/or frequency $\omega$
140 determining throughput speed v of pore 1
150 determining throughput resistance R of pore 1

The invention claimed is:

1. A method to determine the throughput speed v of a pore, comprising the steps of:
feeding, by means of a driving force F, a filiform calibration element through the pore, the calibration element having a plurality of markers spaced apart by known distances and configured to produce an interaction event that transmits a signal away from the pore upon interaction with the pore;
detecting a plurality of interaction events;
determining a time interval $\Delta t$ between successive interaction events, and/or a frequency $\omega$ of interaction events;
determining, from the known distances and from the time interval $\Delta t$ and/or the frequency $\omega$, the speed with which the filiform calibration element passes through the pore as the throughput speed v; and
further comprising: determining a throughput resistance R of the pore as a ratio of the speed v per unit of the driving force F.

2. A method to determine the throughput speed v of a pore, comprising the steps of:
feeding, by means of a driving force F, a filiform calibration element through the pore, the calibration element having a plurality of markers spaced apart by known distances and configured to produce an interaction event that transmits a signal away from the pore upon interaction with the pore;
detecting a plurality of interaction events;
determining a time interval $\Delta t$ between successive interaction events, and/or a frequency $\omega$ of interaction events; and
detecting at least one increase in the mechanical resistance that the filiform calibration element experiences when moving through the pore as an interaction event.

3. A method to determine the throughput speed v of a pore, comprising the steps of:
feeding, by means of a driving force F, a filiform calibration element through the pore, the calibration element having a plurality of markers spaced apart by known distances and configured to produce an interaction event that transmits a signal away from the pore upon interaction with the pore;
detecting a plurality of interaction events;
determining a time interval $\Delta t$ between successive interaction events, and/or a frequency $\omega$ of interaction events; and
measuring an intensity of light that is emitted from a marker with a detector outside the pore, and
detecting at least one change of the intensity as an interaction event.

4. The method of claim 3, wherein the change of the intensity is an increase of the intensity that results from an amplification of the light by the inner wall of the pore, or an extinction of the light produced by the inner wall of the pore.

5. A method to determine the throughput speed v of a pore, comprising the steps of:
feeding, by means of a driving force F, a filiform calibration element through the pore, the calibration element having a plurality of markers spaced apart by known distances and configured to produce an interaction event that transmits a signal away from the pore upon interaction with the pore;
detecting a plurality of interaction events;
determining a time interval $\Delta t$ between successive interaction events, and/or a frequency $\omega$ of interaction events; and
wherein the feeding a filiform calibration element specifically comprises:
contacting the pore with a liquid solution comprising a plurality of filiform calibration elements.

6. A method to determine the throughput speed v of a pore, comprising the steps of:
- feeding, by means of a driving force F, a filiform calibration element through the pore, the calibration element having a plurality of markers spaced apart by known distances and configured to produce an interaction event that transmits a signal away from the pore upon interaction with the pore;
- detecting a plurality of interaction events;
- determining a time interval At between successive interaction events, and/or a frequency $\omega$ of interaction events; and
- wherein the driving force F specifically comprises one or more of:
  - a pressure gradient, a concentration gradient, and an electrostatic force.

7. A filiform calibration element, the filiform calibration element comprising:
- a strand;
- a plurality of light sources coupled to the strand,
- wherein the filiform calibration element is configured to pass through a pore of at most 5 µm diameter,
- wherein the plurality of light sources are configured to absorb excitation light of a first wavelength $\lambda_1$ and to emit light of a second wavelength $\lambda_2$ in response to the excitation light, as markers,
- wherein the light sources are quantum dots, and
- wherein the strand is a DNA strand with at least one sticky end, at least one quantum dot is coupled to a counterpart of the sticky end by means of a thiol group, and the counterpart is attached to the sticky end of the DNA strand.

8. A filiform calibration element, the filiform calibration element comprising:
- a strand;
- a plurality of light sources coupled to the strand,
- wherein the plurality of light sources are configured to absorb excitation light of a first wavelength $\lambda_1$ and to emit light of a second wavelength $\lambda_2$ in response to the excitation light, as markers, and
- wherein the filiform calibration element is configured to pass through a pore of at most 200 nm diameter.

9. A filiform calibration element, the filiform calibration element comprising:
- a strand;
- a plurality of light sources coupled to the strand,
- wherein the filiform calibration element is configured to pass through a pore of at most 5 µm diameter,
- wherein the plurality of light sources are configured to absorb excitation light of a first wavelength $\lambda_1$ and to emit light of a second wavelength $\lambda_2$ in response to the excitation light, as markers, and
- wherein the filiform calibration element is further functionalized to be electronegative, so as to facilitate the driving of the filiform calibration element through the pore by means of an electrostatic driving force F.

10. A liquid solution as a tool for determining the throughput speed v of at least one pore, comprising:
- a solvent and a plurality of filiform calibration elements comprising:
- a strand;
- a plurality of light sources coupled to the strand,
- wherein the filiform calibration element is configured to pass through a pore of at most 5 µm diameter, and
- wherein the plurality of light sources are configured to absorb excitation light of a first wavelength $\lambda_1$ and to emit light of a second wavelength $\lambda_2$ in response to the excitation light, as markers.

11. The liquid solution of claim 10, wherein the solvent comprises buffered KCl.

12. The liquid solution of claim 11, wherein the concentration of the buffered KCl is up to 1 M KCl and the concentration of filiform calibration elements is between a few fM to hundreds of nM.

* * * * *

UNITED STATES PATENT AND TRADEMARK OFFICE
CERTIFICATE OF CORRECTION

PATENT NO. : 11,698,363 B2
APPLICATION NO. : 16/632296
DATED : July 11, 2023
INVENTOR(S) : Robert Blick et al.

It is certified that error appears in the above-identified patent and that said Letters Patent is hereby corrected as shown below:

In the Specification

Column 1, Line 53, "Alum" should be --Aluru--.

Signed and Sealed this
Seventeenth Day of October, 2023

Katherine Kelly Vidal
*Director of the United States Patent and Trademark Office*